United States Patent
Talley

(10) Patent No.: US 10,662,219 B2
(45) Date of Patent: May 26, 2020

(54) FUROSTAN-3-OL DERIVATIVES AS SKELETAL MUSCLE HYPERTROPHIC AGENTS

(71) Applicant: EMMYON, INC., Coralville, IA (US)

(72) Inventor: John J Talley, St. Louis, MO (US)

(73) Assignee: EMMYON, INC., Coralville, IA (US)

( * ) Notice: Subject to any disclaimer, the term of this patent is extended or adjusted under 35 U.S.C. 154(b) by 0 days.

(21) Appl. No.: 15/769,428

(22) PCT Filed: Oct. 28, 2016

(86) PCT No.: PCT/US2016/059264
§ 371 (c)(1),
(2) Date: Apr. 19, 2018

(87) PCT Pub. No.: WO2017/075313
PCT Pub. Date: May 4, 2017

(65) Prior Publication Data
US 2018/0305399 A1 Oct. 25, 2018

Related U.S. Application Data

(60) Provisional application No. 62/247,968, filed on Oct. 29, 2015.

(51) Int. Cl.
| C07J 71/00 | (2006.01) |
| A61P 21/00 | (2006.01) |
| A61P 21/06 | (2006.01) |
| C07D 307/77 | (2006.01) |
| A61K 31/343 | (2006.01) |

(52) U.S. Cl.
CPC .......... *C07J 71/0005* (2013.01); *A61P 21/00* (2018.01); *A61P 21/06* (2018.01); *C07D 307/77* (2013.01); *A61K 31/343* (2013.01)

(58) Field of Classification Search
CPC ........ C07J 71/0005; A61P 21/00; A61P 21/06
See application file for complete search history.

(56) References Cited

U.S. PATENT DOCUMENTS

| 2008/0299220 A1 | 12/2008 | Tamarkin et al. |
| 2014/0018312 A1 | 1/2014 | Malouin et al. |
| 2015/0164918 A1 | 6/2015 | Adams et al. |

FOREIGN PATENT DOCUMENTS

| CN | 104513289 A | * | 4/2015 |
| WO | 2007003948 A2 | | 1/2007 |
| WO | 2012170546 A1 | | 12/2012 |
| WO | 2014022772 A1 | | 2/2014 |

OTHER PUBLICATIONS

Uhle,F. "The Synthesis of Azaoxaspirane Steroid Alkaloids" J. Am. Chem. Soc.,1961, 83(6),pp. 1460-1472. (Year: 1961).*

Matsushita et al. "Efficient Conversion of Tomatidine into Neuritogenic Pregnane Derivative", Chem.Parm.Bull, 2007, vol. 55(7), pp. 1077-1078. (Year: 2007).*

Machine translation of CN 104513289A acquired Jun. 9, 2019 (Year: 2019).*

Sato et al. J. Amer. Chem. Soc., 1960, vol. 25, pp. 783-786.*

Matsushita et al. Chem. Pharm. Bull. 2007, vol. 55, No. 7, pp. 1077-1078.*

International Search Report and Written Opinion issued in PCT/US2016/059264, dated Jan. 17, 2017.

Dyle et al., "Systems-based Discovery of Tomatidine as a Natural Small Molecule Inhibitor of Skeletal Muscle Atrophy," The Journal of Biological Chemistry, May 23, 2014, vol. 289, No. 21, pp. 14913-14924.

Goswami et al., "A One-Pot Efficient Process for 16-Dehydropregnenolone Acetate," Organic Process Research & Development, 2003, vol. 7, No. 3, pp. 306-308.

Chagnon, et al., Unraveling the structure—activity relationship of tomatidine, a steroid alkaloid with unique antibiotic properties against persistent forms of Staphylococcus aureus, Elsevier, European Journal of Medicinal Chemistry, 80, pp. 605-620 2014.

Schreiber, Abbau Von Soladulcidin and Tomatidin Zu Den Enantiomerer 5-Methyl-Piperidonen-(2), Solanum-Alkaloide, XLVIII, pp. 219, 227 1965.

Sato, et al., The Chemistry of the Spiroaminoketal Side Chain of Solasodine and Tomatidine. I. Improved Preparation of 3ß-Acetoxy-5, 16-pregnadien-20-one and 3ß-Acetoxy-5a-pregn-16-en-20-one from Solasodine and Tomatidine, https://pubs.acs.org/doi/10.1021/jo01075a028, contribution from the National Institute of Arthritis and Metabolic Diseases, National Institutes of Health, Public Health Service, U.S. Department of Health, Education, and Welfare, pp. 783-786 Sep. 24, 1959.

Extended European Search Report for European Application No. 16860856.0 dated Jun. 6, 2019.

* cited by examiner

*Primary Examiner* — Samira J Jean-Louis
(74) *Attorney, Agent, or Firm* — Heslin Rothenberg Farley & Mesiti, P.C.

(57) ABSTRACT

Compounds of formula I

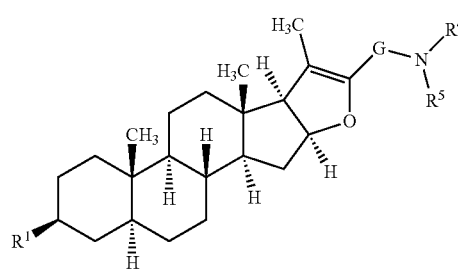

are disclosed. The compounds are useful for promoting skeletal muscle hypertrophy or treating skeletal muscle atrophy.

28 Claims, No Drawings

FUROSTAN-3-OL DERIVATIVES AS SKELETAL MUSCLE HYPERTROPHIC AGENTS

CROSS REFERENCE TO RELATED APPLICATIONS

This application is a national phase filing under 35 U.S.C. § 371 of PCT International Application PCT/US2016/059264, filed Oct. 28, 2016. PCT/US2016/059264 claimed priority from U.S. Provisional Application No. 62/247,968, filed Oct. 29, 2015. The contents of each of the prior applications are incorporated by reference herein in their entirety.

FEDERALLY SPONSORED RESEARCH

This invention was made with Government support under contract 1R41AG047684-01 awarded by the National Institutes of Health. The Government has certain rights in the invention.

FIELD OF THE INVENTION

The invention relates to furostan-3-ol derivatives described in systematic nomenclature as 10-substituted hexadecahydro-1H-naphtho[2',1':4,5]indeno[2,1-b]furan-4-ols and hexadecahydro-1H-naphtho[2',1':4,5]indeno[2,1-b]furan-4-amines. The compounds are useful for treating muscle atrophy and as muscle hypertrophic agents.

BACKGROUND

Skeletal muscle atrophy is characteristic of starvation and a common effect of aging. It is also a nearly universal consequence of severe human illnesses, including cancer, chronic renal failure, congestive heart failure, chronic respiratory disease, insulin deficiency, acute critical illness, chronic infections such as HIV/AIDS, muscle denervation, and many other medical and surgical conditions. Prior to 2010, medical therapies to prevent or reverse skeletal muscle atrophy in human patients did not exist. As a result, millions of individuals suffered sequelae of muscle atrophy, including weakness, falls, fatigue, impaired recovery from illness and injury, fractures, and loss of independence. The burden that skeletal muscle atrophy places on individuals, their families, and society in general, is tremendous.

The pathogenesis of skeletal muscle atrophy was not formerly well understood, but important advances have been made. For example, it has been described previously that insulin/IGF1 signaling promotes muscle hypertrophy and inhibits muscle atrophy, but is reduced by atrophy-inducing stresses such as fasting or muscle denervation (Bodine S C, et al. (2001) *Nat Cell Biol* 3(11):1014-1019; Sandri M, et al. (2004) *Cell* 117(3):399-4121; Stitt T N, et al. (2004) *Mol Cell* 14(3):395-403; Hu Z, et al. (2009) *The Journal of clinical investigation* 119(10):3059-3069; Dobrowolny G, et al. (2005) *The Journal of cell biology* 168(2):193-199; Kandarian S C & Jackman R W (2006) *Muscle & nerve* 33(2):155-165; Hirose M, et al. (2001) *Metabolism: clinical and experimental* 50(2):216-222; Pallafacchina G, et al. (2002) *Proceedings of the National Academy of Sciences of the United States of America* 99(14):9213-9218). The hypertrophic and anti-atrophic effects of insulin/IGF1 signaling are mediated at least in part through increased activity of phosphoinositide 3-kinase (PI3K) and its downstream effectors, including Akt and mammalian target of rapamycin complex 1 (mTORC1) Sandri M (2008) *Physiology (Bethesda)* 23:160-170; Glass D J (2005) *The international journal of biochemistry & cell biology* 37(10): 1974-1984).

Another important advance came from microarray studies of atrophying rodent muscle (Lecker S H, et al. (2004) *Faseb J* 18(1):39-51; Sacheck J M, et al. (2007) *Faseb J* 21(1): 140-155; Jagoe R T, et al. *Faseb J* 16(13): 1697-1712). Those studies showed that several seemingly disparate atrophy-inducing stresses (including fasting, muscle denervation and severe systemic illness) generated many common changes in skeletal muscle mRNA expression. Some of those atrophy-associated changes promote muscle atrophy in mice; these include induction of the mRNAs encoding atroginI/MAFbx and MuRF1 (two E3 ubiquitin ligases that catalyze proteolytic events), and repression of the mRNA encoding PGC-1α (a transcriptional co-activator that inhibits muscle atrophy) (Sandri M, et al. (2006) *Proceedings of the National Academy of Sciences of the United States of America* 103(44): 16260-16265; Wenz T, et al. *Proceedings of the National Academy of Sciences of the United States of America* 106(48):20405-20410; Bodine S C, et al. (2001) *Science* (New York, N.Y. 294(5547): 1704-1708; Lagirand-Cantaloube J, et al. (2008) *The EMBO journal* 27(8): 1266-1276; Cohen S, et al. (2009) *The Journal of cell biology* 185(6):1083-1095; Adams V, et al. (2008) *Journal of molecular biology* 384(1):48-59). However, the roles of many other mRNAs that are increased or decreased in atrophying rodent muscle are not yet defined. Data on the mechanisms of human muscle atrophy are even more limited, although atrogin-1 and MuRF1 are likely to be involved (Leger B, et al. (2006) *Faseb J* 20(3):583-585; Doucet M, et al. (2007) *American journal of respiratory and critical care medicine* 176(3):261-269; Levine S, et al. (2008) *The New England journal of medicine* 358(13): 1327-1335).

In 2010 results began appearing from the laboratory of Christopher Adams at the University of Iowa; these are reflected in published US applications 2013/0203712, 2014/0228333, 2014/0371188 and 2015/0164918. These breakthrough studies provided evidence that small molecule therapeutics were capable of increasing skeletal muscle mass and strength in vivo.

The furostanol scaffold of the compounds described below is found primarily in the aglycone portion of plant saponins. The plant saponins are frequently associated in the literature with various biological activities, but therapeutic properties are not commonly ascribed to the unglycosylated furostanol sapogenins. For example, US published application 2007/0254847 describes a class of saponins obtained from *Dioscorea panthaica* and *Dioscorea nipponica* which are said to possess utility in treating cerebrovascular and coronary heart diseases. Although the glycosides share a furostanol core, it is the glycoside saponin, not the furostanol aglycone to which the utility is ascribed.

SUMMARY OF THE INVENTION

In one aspect, the invention relates to compounds of formula I

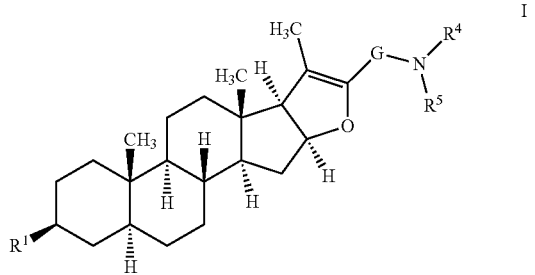

I wherein:

$R^1$ is chosen from $OR^2$ and $NHR^3$;
$R^2$ is H or acetyl;
$R^3$ is chosen from —$(CH_2)_n$OH and —$(CH_2CH_2O)_n$H;
G is $(C_2$-$C_{10})$hydrocarbyl;
$R^4$ is H or $(C_1$-$C_3)$hydrocarbyl; and
$R^5$ is chosen from H, $(C_1$-$C_{10})$hydrocarbyl, fluoro$(C_1$-$C_6)$ alkyl, and —C(=O)$R^6$,
wherein $R^6$ is chosen from H, $(C_1$-$C_{10})$aliphatic hydrocarbyl, —O—$(C_1$-$C_{10})$hydrocarbyl, —NH—$(C_1$-$C_{10})$hydrocarbyl, substituted aryl, substituted arylalkyl, heterocyclyl, substituted heteroaryl, heteroarylalkyl, substituted heteroarylalkyl, —NH-(substituted aryl), —NH-(substituted arylalkyl), —NH-(heterocyclyl), and —NH-(substituted heteroaryl);
wherein substituents on aryl and heteroaryl are chosen from halogen, halo$(C_1$-$C_6)$alkyl, $(C_1$-$C_6)$alkyl, $(C_1$-$C_6)$acyl, $(C_1$-$C_6)$alkoxy$(C_1$-$C_6)$alkyl, hydroxy$(C_1$-$C_6)$alkyl, phenyl, heteroaryl, benzenesulfonyl, hydroxy, halo$(C_1$-$C_6)$alkoxy, $(C_1$-$C_6)$oxaalkyl, carboxy, $(C_1$-$C_6)$alkoxycarbonyl [—C(=O)O-alkyl], $(C_1$-$C_6)$alkoxycarbonylamino [HNC(=O)O-alkyl], carboxamido [—C(=O)NH$_2$], $(C_1$-$C_6)$alkylaminocarbonyl [—C(=O)NH-alkyl], cyano, acetoxy, nitro, amino, $(C_1$-$C_6)$ alkylamino, di$(C_1$-$C_6)$alkylamino, di$(C_1$-$C_6)$alkylamino$(C_1$-$C_6)$alkyl, mercapto, $(C_1$-$C_6)$alkylthio, $(C_1$-$C_6)$alkylsulfone, sulfonylamino, $(C_1$-$C_6)$alkylsulfinyl, $(C_1$-$C_6)$alkylsulfonyl, $(C_1$-$C_6)$acylamino$(C_1$-$C_6)$alkyl, $(C_1$-$C_6)$acylamino, amidino, heterocyclyl, phenoxy, benzyloxy, heteroaryloxy, hydroxyimino, alkoxyimino, aminosulfonyl, guanidino and ureido; and
n is 2-6.

In a second aspect, the invention relates to pharmaceutical compositions comprising a pharmaceutically acceptable carrier and any compound falling within the genus I.

In a third aspect, the invention relates to a method for reducing skeletal muscle atrophy or promoting skeletal muscle hypertrophy. The method comprises administering to a mammal a compound falling within the genus of formula I.

DETAILED DESCRIPTION OF THE INVENTION

In the first, composition aspect, the invention relates to compounds of formula I

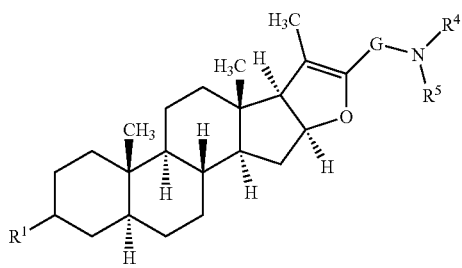

In these compounds, $R^1$ may be chosen from $OR^2$ and $NHR^3$. In one embodiment, $R^1$ is $NHR^3$; in another $R^1$ is $OR^2$. The carbon to which $R^1$ is attached is preferably of the (S) absolute configuration, particularly when $R^1$ is $OR^2$. $R^3$ is hydroxy$(C_2$-$C_6)$alkyl or hydroxy oxa$(C_3$-$C_{18})$alkyl, preferably —$CH_2CH_2$OH.

G may be $(C_2$-$C_{10})$hydrocarbyl. In some embodiments, G may be linear or branched $(C_4$-$C_7)$alkyl. In one embodiment, G is branched $(C_5)$alkyl. In a further embodiment G is —$CH_2CH_2CH(CH_3)CH_2$—.

$R^4$ may be H or $(C_1$-$C_3)$hydrocarbyl. In some embodiments, $R^4$ is $CH_3$; in others $R^4$ is hydrogen.

$R^5$ may be hydrogen, $(C_1$-$C_{10})$hydrocarbyl, fluoro$(C_1$-$C_6)$ alkyl, and —C(=O)$R^6$. In some embodiments, $R^5$ is chosen from H, $(C_1$-$C_6)$alkyl, and fluoro$(C_1$-$C_6)$alkyl. In some embodiments, $R^5$ is H. In other embodiments, $R^5$ may be methyl, ethyl, propyl, (including isopropyl), butyl (including n-butyl, sec-butyl, isobutyl, and t-butyl) or their fluorinated congeners, i.e. $CF_3$, $C_2F_5$, $C_2H_2F_3$, $C_3F_7$, $C_3H_4F_3$, $C_3H_5F_2$, $C_4F_9$, etc. In other embodiments, $R^5$ may be —C(=O)$R^6$.

$R^6$ may be H, $(C_1$-$C_{10})$hydrocarbyl, —O—$(C_1$-$C_{10})$hydrocarbyl, —NH—$(C_1$-$C_{10})$hydrocarbyl, substituted aryl, substituted arylalkyl, heterocyclyl, substituted heteroaryl, heteroarylalkyl, substituted heteroarylalkyl, —NH-(substituted aryl), —NH-(substituted arylalkyl), —NH-(heterocyclyl), or —NH-(substituted heteroaryl). In some embodiments, $R^6$ is H, $(C_1$-$C_{10})$hydrocarbyl, or —O—$(C_1$-$C_{10})$hydrocarbyl. In further embodiments, $R^6$ is $(C_1$-$C_6)$alkyl or —O$(C_1$-$C_6)$ alkyl.

Hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, and the like Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, § 196, but without the restriction of § 127(a)], i.e. it refers to compounds in which the oxygen is bonded via a single bond to its adjacent atoms (forming ether bonds); it does not refer to doubly bonded oxygen, as would be found in carbonyl groups.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include formyl, acetyl, benzoyl, propionyl, isobutyryl and the like. Lower-acyl refers to groups containing one to four carbons. The double bonded oxygen, when referred to as a substituent itself is called "oxo".

The term "aryl" as used herein is a group that contains any carbon-based aromatic group including, but not limited to, benzene, naphthalene, phenyl, biphenyl, phenoxybenzene, and the like.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

These and other materials are disclosed herein, and it is understood that when combinations, subsets, interactions, groups, etc. of these materials are disclosed, while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

In another aspect, the invention relates to the use of the compounds of formula I in medicine. In methods of the invention, the term "subject" refers to the target of administration, e.g. an animal. Thus the subject of the herein disclosed methods can be a vertebrate, such as a mammal, a fish, a bird, a reptile, or an amphibian. More specifically, the subject of the herein disclosed methods can be a human, non-human primate, horse, pig, rabbit, dog, sheep, goat, cow, cat, guinea pig, fish, bird, or rodent. A patient refers to a subject afflicted with a disease or disorder, e.g. muscular atrophy. The term "patient" includes human and veterinary subjects.

As used herein, the term "treatment" refers to the medical management of a patient with the intent to cure, ameliorate, palliate, stabilize, or forestall a disease, pathological condition, or disorder. This term includes palliative treatment, that is, treatment designed for the relief of symptoms rather than the curing of the disease, pathological condition, or disorder; treatment directed to minimizing or partially or completely inhibiting the development of the associated disease and supportive treatment, that is, treatment employed to supplement another specific therapy directed toward the improvement of the associated disease. Aspects of the invention include the use for asthetic and self-improvement purposes rather than for curing, ameliorating, or forestalling a disease. For example, such uses include, but are not limited to, the administration of the disclosed compound in nutraceuticals, medicinal foods, functional foods, energy bars, energy drinks, sports drinks, protein bars, protein powders, tea, coffee, milk, milk products, cereal, oatmeal, infant formulas, supplements (such as multivitamins) or chewing gum.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient. It should be understood that in addition to the ingredients particularly mentioned above, the formulations of this invention may include other agents conventional in the art having regard to the type of formulation in question, for example those suitable for oral administration may include flavoring agents.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, betulinic, boric, butyric, camphoric, camphorsulfonic, carbonic, citric, ethanedisulfonic, ethanesulfonic, ethyl enediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, ursolic and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

In the treatment conditions which require modulation of cellular function related to muscle health, muscle function and/or healthy muscle aging an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient.

Muscle hypertrophy is defined as the increase in muscle size or mass of the muscle, and can include an increase in individual fiber volume and/or an increase in the cross-sectional area of myofibers, and may also include an increase in the number of nuclei per muscle fiber. Muscle hypertrophy can also include an increase in the volume and mass of whole muscles; however, muscle hypertrophy can be differentiated from muscle hyperplasia, which is an increased number of muscle fibers. In one embodiment, muscular hypertrophy refers to an increase in the number of actin and myosin contractile proteins. Muscle hypertrophy leads to an increase in muscle strength. The muscle can be skeletal muscle.

In another aspect, the invention relates to neutraceutical compositions comprising a neutraceutically acceptable carrier and a compound of formula I, wherein the compound is present in an effective amount. The compound may be present in an amount greater than 5 mg, 10 mg, 25 mg, 50 mg, 100 mg, 150 mg, 200 mg, 250 mg, 300 mg, 400, mg, 500 mg, 750 mg, 1000 mg, 1,500 mg, or 2,000 mg.

Muscle atrophy is defined as a decrease in the mass of the muscle; it can be a partial or complete wasting away of muscle. When a muscle atrophies, this leads to muscle weakness, since the ability to exert force is related to mass. Muscle atrophy is a co-morbidity of several common diseases, and patients who have "cachexia" in these disease settings have a poor prognosis. There are many diseases and conditions which cause muscle atrophy, including malnutrition, bed rest, neurologic disease (including multiple sclerosis, amyotrophic lateral sclerosis, spinal muscular atrophy, critical illness neuropathy, spinal cord injury or peripheral nerve injury), orthopedic injury, joint repair, joint replacement, casting, and other post-surgical forms of limb immobilization, osteoarthritis, chronic disease (including cancer, congestive heart failure, chronic pulmonary disease, chronic renal failure, chronic liver disease, diabetes mellitus, rheumatoid arthritis, Cushing syndrome, growth hormone deficiency, IGF-I deficiency, hypogonadism and chronic infections such as HIV/AIDS or tuberculosis), burns, sepsis, other illnesses requiring mechanical ventilation, drug-induced muscle disease (such as glucorticoid-induced myopathy, statin-induced myopathy, and muscle atrophy secondary to anti-androgen therapies or cancer chemotherapy), genetic diseases that primarily affect skeletal muscle (such as muscular dystrophy and myotonic dystrophy), autoimmune diseases that affect skeletal muscle (such as polymyositis and dermatomyositis), other primary muscle diseases such as inclusion body myositis, spaceflight, and aging. Muscle atrophy is believed to occur by a change in the normal balance between protein synthesis and protein degradation. During atrophy, there is a down-regulation of protein synthesis pathways, and an activation of protein breakdown pathways. The particular protein degradation pathway which seems to be responsible for much of the muscle loss seen in a muscle undergoing atrophy is the ATP-dependent, ubiquitin/proteasome pathway.

The compounds disclosed herein are useful for promoting or increasing muscle hypertrophy. The compounds are also useful for increasing muscle mass, increasing muscle hypertrophy, increasing muscle strength, increasing muscle endurance, increasing muscle quality, reducing muscle weakness and fatigue, increasing cellular protein, and promoting growth of muscle cells. In addition to their utility in human therapy, the compounds may be used to increase muscle mass in domesticated animals, such as animals suitable for meat production. Animals suitable for meat production include, but are not limited to cows, bulls, bison, horses, sheep, goats, pigs, ducks, geese, lamas, camels, dromedary, boars, turkeys, and chickens.

The following examples are put forth so as to provide those of ordinary skill in the art with a complete disclosure and description of how the compounds, compositions, and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Certain materials, reagents and kits were obtained from specific vendors as indicated below, and as appropriate the vendor catalog, part or other number specifying the item are indicated. Vendors indicated below are as follows: "Pierce" is Pierce Biotechnology, Inc., Milwaukee, Wis., USA, a division of Thermo Fisher Scientific, Inc.; "Roche Diagnostics" is Roche Diagnostics Corporation, Indianapolis, Ind., USA; and, "Sigma" is Sigma-Aldrich Corporation, Saint Louis, Mo., USA. Unless indicated otherwise, parts are parts by weight, temperature is in ° C. or is at ambient temperature, and pressure is at or near atmospheric.

Compounds of the invention were synthesized as follows:

Example 1. (2aS,4S,6aS,6bS,8aS,8bS,11aS,12aS, 12bR)-10-((S)-4-acetamido-3-methylbutyl)-6a,8a,9-trimethyl-2,2a,3,4,5,6,6a,6b,7,8,8a,8b,11a,12,12a, 12b-hexadecahydro-1H-naphtho[2',1':4,5]indeno[2, 1-b]furan-4-yl acetate

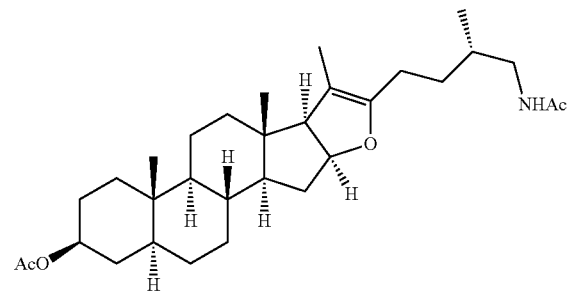

Tomatidine hydrochloride (200 mg, 0.44 mmol), pyridine (8 mL), and acetic anhydride (4 mL) were allowed to stir at room temperature for 18 h. The solution was diluted with water and extracted with 3 times with ethyl acetate; the combined extracts were washed with 3N aq. HCl and dried over anhyd. MgSO$_4$, concentrated in vacuo and the residue purified by flash chromatography eluting with hexanes and ethyl acetate to afford 35 mg of the title compound as an amorphous solid, 16%. $^1$H NMR (400 MHz, CDCl$_3$) and $^{13}$C NMR (100 MHz, CDCl$_3$) were consistent. LC t$_r$=6.0 min (C-18 column, 5 to 95% acetonitrile/water over 6 min at 1.7 mL/min with detection 210 nm, at 23° C.). ES(pos)MS m/z 500 (M+H calcd for C$_{31}$H$_{50}$NO$_4$ requires 500).

Example 2 tert-Butyl ((S)-4-((2aS,4S,6aS,6bS,8aS, 8bS,11aS,12aS,12bR)-4-hydroxy-6a,8a,9-trimethyl-2,2a,3,4,5,6,6a,6b,7,8,8a,8b,11a,12,12a,12b-hexadecahydro-1H-naphtho[2',1':4,5]indeno[2,1-b]furan-10-yl)-2-methylbutyl)carbamate

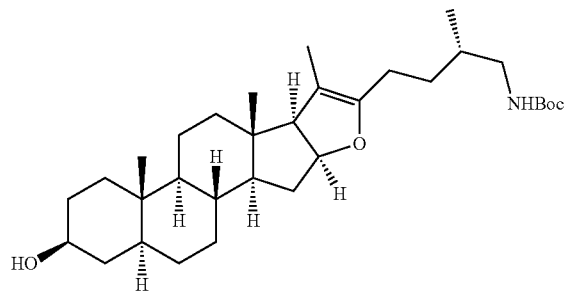

A solution of tomatidine hydrochloride (250 mg, 0.55 mmol), di-tert-butyl dicarbonate (152 µL, 0.66 mmol), potassium carbonate (182 mg, 1.32 mmol) in 1 mL of 1,4-dioxane were stirred at 50° C. for 18 h. The solution was diluted with water and extracted with 3 times with ether; the combined extracts were washed with water, brine, dried over anhyd. MgSO$_4$, concentrated in vacuo, and the residue purified by flash chromatography eluting with hexanes and ethyl acetate to afford 215 mg of the title compound as an white solid, 76%. $^1$H NMR (400 MHz, CDCl$_3$) and $^{13}$C NMR (100 MHz, CDCl$_3$) were consistent. LC t$_r$=7.8 min (C-18 column, 5 to 95% acetonitrile/water over 6 min at 1.7 mL/min with detection 210 nm, at 23° C.). ES(pos)MS m/z 516 (M+H calcd for C$_{32}$H$_{54}$NO$_4$ requires 516).

Example 3. (2aS,4S,6aS,6bS,8aS,8bS,11aS,12aS, 12bR)-10-((S)-4-Amino-3-methylbutyl)-6a,8a,9-trimethyl-2,2a,3,4,5,6,6a,6b,7,8,8a,8b,11a,12,12a, 12b-hexadecahydro-1H-naphtho[2',1':4,5]indeno[2, 1-b]furan-4-ol hydrochloride

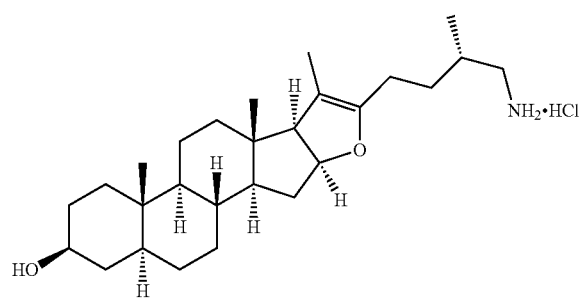

A solution of tert-butyl ((S)-4-((2aS,4S,6aS,6bS,8aS,8bS, 11aS,12aS,12bR)-4-hydroxy-6a,8a,9-trimethyl-2,2a,3,4,5,6, 6a,6b,7,8,8a,8b,11a,12,12a,12b-hexadecahydro-1H-naphtho [2',1':4,5]indeno[2,1-b]furan-10-yl)-2-methylbutyl) carbamate (50 mg, 0.10 mmol) and 1 mL of 4M HCl in 1,4-dioxane for 0.5 h. The solution was concentrated and the residue dissolved in acetonitrile whereupon a precipitate formed that was isolated by filtration and dried in vacuo to afford 33.7 mg of pure product 75%. $^1$H NMR (400 MHz, CDCl$_3$) and $^{13}$C NMR (100 MHz, CD$_3$OD) consistent. LC t$_r$=3.7 min (C-18 column, 5 to 95% acetonitrile/water over 6 min at 1.7 mL/min with detection 210 nm, at 23° C.). ES(pos)MS m/z 416 (M+H calcd for C$_{27}$H$_{46}$NO$_2$ requires 416).

Example 4. (2aS,4S,6aS,6bS,8aS,8bS,11aS,12aS, 12bR)-10-((S)-4-((tert-butoxycarbonyl)amino)-3-methylbutyl)-6a,8a,9-trimethyl-2,2a,3,4,5,6,6a,6b,7, 8,8a,8b,11a,12,12a,12b-hexadecahydro-1H-naphtho [2',1':4,5]indeno[2,1-b]furan-4-yl acetate acetate

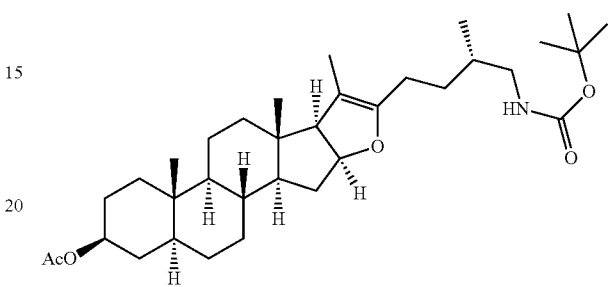

A solution of (2aS,2'S,4S,5'R,6aS,6bS,8aS,8bR,9S,11aS, 12aS,12bR)-tert-butyl 4-hydroxy-5',6a,8a,9-tetramethyloctadecahydrospiro[naphtho[2',1':4,5]indeno[2,1-b]furan-10, 2'-piperidine]-1'-carboxylate (138 mg, 0.268 mmol), triethylamine (56 µL, 0.40 mmol), acetic anhydride (30 µL, 0.32 mmol) were diluted with 1 mL of tetrahydrofuran and allowed to stir for 18 h. The solution was poured into water and extracted with ethyl acetate, dried over anhyd. sodium sulfate, filtered, concentrated in vacuo and the residue subjected to flash chromatography eluting with hexanes and ethyl acetate. The appropriate factions were combined and concentrated in vacuo to afford 100 mg of the title compound as a white foam, 67%. The $^1$H NMR (400 MHz, CDCl$_3$) and $^{13}$C NMR (100 MHz, CDCl$_3$) were consistent. LC t$_r$=8.2 min (C-18 column, 5 to 95% acetonitrile/water over 6 min at 1.7 mL/min with detection 210 nm, at 23° C.). ES(pos)MS m/z 558 (M+H calcd for C$_{34}$H$_{56}$NO$_5$ requires 558).

Example 5. Methyl ((S)-4-((2aS,4S,6aS,6bS,8aS, 8bS,11aS,12aS,12bR)-4-hydroxy-6a,8a,9-trimethyl-2,2a,3,4,5,6,6a,6b,7,8,8a,8b,11a,12,12a,12b-hexadecahydro-1H-naphtho[2',1':4,5]indeno[2,1-b]furan-10-yl)-2-methylbutyl)carbamate

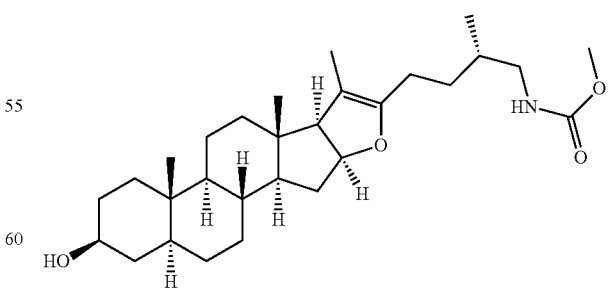

Tomatidine hydrochloride (100 mg, 0.22 mmol), potassium carbonate (92 mg, 0.66 mmol), methyl chloroformate (26 µL, 0.33 mmol) in 450 µL of tetrahydrofuran were stirred at room temperature for 18 h. The solution was poured into water and extracted with ethyl acetate, dried over anhyd. sodium sulfate, filtered, concentrated in vacuo and the residue subjected to flash chromatography eluting with hexanes and ethyl acetate. The appropriate factions were combined and concentrated in vacuo to afford 77 mg of the title compound as a white foam, 73%. The $^1$H NMR (400 MHz, CDCl$_3$) and $^{13}$C NMR (100 MHz, CDCl$_3$) were consistent. LC t$_r$=8.2 min (C-18 column, 5 to 95% acetonitrile/water over 5.98 min at 1.7 mL/min with detection 210 nm, at 23° C.). ES(pos)MS m/z 474 (M+H calcd for C$_{29}$H$_{48}$NO$_4$ requires 474).

Example 6. Isobutyl ((S)-4-((2aS,4S,6aS,6bS,8aS, 8bS,11aS,12aS,12bR)-4-hydroxy-6a,8a,9-trimethyl-2,2a,3,4,5,6,6a,6b,7,8,8a,8b,11a,12,12a,12b-hexadecahydro-1H-naphtho[2',1':4,5]indeno[2,1-b]furan-10-yl)-2-methylbutyl)carbamate

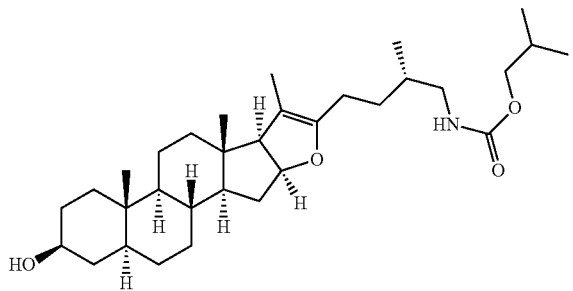

Tomatidine hydrochloride (100 mg, 0.22 mmol), potassium carbonate (92 mg, 0.66 mmol), isobutyl chloroformate (32 µL, 0.33 mmol) in 450 µL of tetrahydrofuran were stirred at room temperature for 18 h. The solution was poured into water and extracted with ethyl acetate, dried over anhyd. sodium sulfate, filtered, concentrated in vacuo and the residue subjected to flash chromatography eluting with hexanes and ethyl acetate. The appropriate factions were combined and concentrated in vacuo to afford 86 mg of the title compound as a white foam, 75%. The $^1$H NMR (400 MHz, CDCl$_3$) and $^{13}$C NMR (100 MHz, CDCl$_3$) were consistent. LC t$_r$=7.1 min (C-18 column, 5 to 95% acetonitrile/water over 5.98 min at 1.7 mL/min with detection 210 nm, at 23° C.). ES(pos)MS m/z 516 (M+H calcd for C$_{32}$H$_{54}$NO$_4$ requires 516).

Example 7. (2aS,4S,6aS,6bS,8aS,8bS,11aS,12aS, 12bR)-10-((S)-4-(Isopropylamino)-3-methylbutyl)-6a,8a,9-trimethyl-2,2a,3,4,5,6,6a,6b,7,8,8a,8b,11a, 12,12a,12b-hexadecahydro-1H-naphtho[2',1':4,5] indeno[2,1-b]furan-4-ol

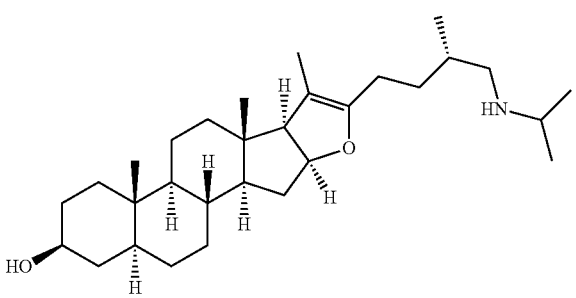

(2aS,4S,6aS,6bS,8aS,8bS,11aS,12aS,12bR)-10-((S)-4-Amino-3-methylbutyl)-6a,8a,9-trimethyl-2,2a,3,4,5,6,6a, 6b,7,8,8a,8b,11a,12,12a,12b-hexadecahydro-1H-naphtho [2',1':4,5]indeno[2,1-b]furan-4-ol hydrochloride (50 mg, 0.11 mmol) was dissolved in 0.5 mL of methanol and then treated sequentially with sodium cyanoborohydride (7.6 mg, 0.12 mmol), and acetone (9.7 µL, 0.13 mmol). The reaction was stirred overnight and then made basic with 1N NaOH and extracted with ethyl acetate. The ethyl acetate extract was washed with water, brine, dried over anhy. MgSO$_4$, filtered and concentrated in vacuo. The residue was purified by flash chromatography eluting with methanol and dichloromethane. The appropriate fractions were collected and concentrated in vacuo to provide 18.4 mg of the title compound as a white solid, 37%. $^1$H NMR (400 MHz, CDCl$_3$) and $^{13}$C NMR (100 MHz, CDCl$_3$) were consistent. LC t$_r$=3.9 min (C-18 column, 5 to 95% acetonitrile/water over 6 min at 1.7 mL/min with detection 210 nm, at 23° C.). ES(pos)MS m/z 458 (M+H calcd for C$_{30}$H$_{52}$NO$_2$ requires 458).

Example 8. (2aS,4S,6aS,6bS,8aS,8bS,11aS,12aS, 12bR)-10-((S)-4-(Dimethylamino)-3-methylbutyl)-6a,8a,9-trimethyl-2,2a,3,4,5,6,6a,6b,7,8,8a,8b,11a, 12,12a,12b-hexadecahydro-1H-naphtho[2',1':4,5] indeno[2,1-b]furan-4-ol

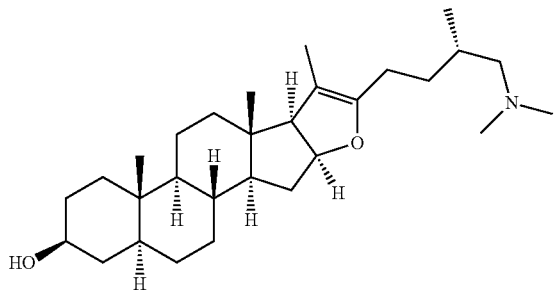

(2aS,4S,6aS,6bS,8aS,8bS,11aS,12aS,12bR)-10-((S)-4-Amino-3-methylbutyl)-6a,8a,9-trimethyl-2,2a,3,4,5,6,6a, 6b,7,8,8a,8b,11a,12,12a,12b-hexadecahydro-1H-naphtho [2',1':4,5]indeno[2,1-b]furan-4-ol hydrochloride (100 mg, 0.22 mmol) was dissolved in 1.0 mL of methanol and then treated sequentially with sodium cyanoborohydride (15.2 mg, 0.24 mmol), and paraformaldehyde (50 mg, 1.67 mmol). The reaction was stirred overnight and then made basic with 1N NaOH and extracted with ethyl acetate. The ethyl acetate extract was washed with water, brine, dried over anhy. MgSO$_4$, filtered and concentrated in vacuo. The residue was purified by flash chromatography eluting with methanol and dichloromethane. The appropriate fractions were collected and concentrated in vacuo to provide 47.9 mg of the title compound as a white solid, 49%. $^1$H NMR (400 MHz, CDCl$_3$) and $^{13}$C NMR (100 MHz, CDCl$_3$) were consistent. LC t$_r$=3.75 min (C-18 column, 5 to 95% acetonitrile/water over 6 min at 1.7 mL/min with detection 210 nm, at 23° C.). ES(pos)MS m/z 444 (M+H calcd for C$_{29}$H$_{50}$NO$_2$ requires 444).

Example 9. (2aS,4S,6aS,6bS,8aS,8bS,11aS,12aS, 12bR)-10-((3S)-4-(((1,1-Difluoropropan-2-yl)amino)-3-methylbutyl)-6a,8a,9-trimethyl-2,2a,3,4,5,6,6a,6b, 7,8,8a,8b,11a,12,12a,12b-hexadecahydro-1H-naphtho[2',1':4,5]indeno[2,1-b]furan-4-ol

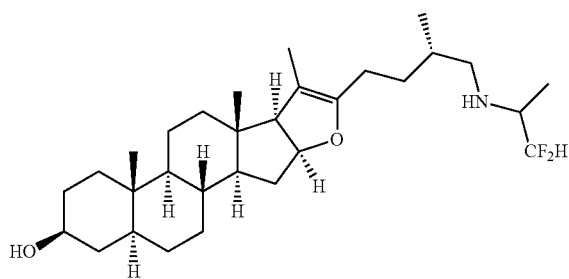

(2aS,4S,6aS,6bS,8aS,8bS,11aS,12aS,12bR)-10-((S)-4-Amino-3-methylbutyl)-6a,8a,9-trimethyl-2,2a,3,4,5,6,6a, 6b,7,8,8a,8b,11a,12,12a,12b-hexadecahydro-1H-naphtho [2',1':4,5]indeno[2,1-b]furan-4-ol hydrochloride (60 mg, 0.13 mmol) was dissolved in 0.5 mL of methanol and then treated sequentially with sodium cyanoborohydride (9 mg, 0.14 mmol), and 1,1-difluoro-propan-2-one (13 μL, 0.16 mmol). The reaction was stirred overnight and then made basic with 1N NaOH and extracted with ethyl acetate. The ethyl acetate extract was washed with water, brine, dried over anhy. MgSO$_4$, filtered and concentrated in vacuo. The residue was purified by flash chromatography eluting with methanol and dichloromethane. The appropriate fractions were collected and concentrated in vacuo to provide 32.7 mg of the title compound as a white solid, 51%. $^1$H NMR (400 MHz, CDCl$_3$), $^{13}$C NMR (100 MHz, CDCl$_3$) and $^{19}$F (376 MHz NMR, CDCl$_3$) were consistent. LC t$_r$=4.05 min (C-18 column, 5 to 95% acetonitrile/water over 6 min at 1.7 mL/min with detection 210 nm, at 23° C.). ES(pos)MS m/z 494 (M+H calcd for C$_{30}$H$_{50}$F$_2$NO$_2$ requires 494).

Example 10. tert-Butyl ((2S)-4-((2aS,6aS,6bS,8aS, 8bS,11aS,12aS,12bR)-4-((2-hydroxyethyl)amino)-6a,8a,9-trimethyl-2,2a,3,4,5,6,6a,6b,7,8,8a,8b,11a, 12,12a,12b-hexadecahydro-1H-naphtho[2',1': 4,5] indeno[2,1-b]furan-10-yl)-2-methylbutyl)carbamate

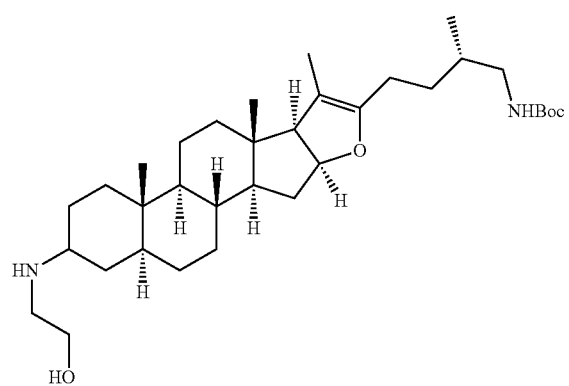

Step 1: tert-Butyl ((S)-4-((2aS,4S,6aS,6bS,8aS,8bS,11aS, 12aS,12bR)-4-hydroxy-6a,8a,9-trimethyl-2,2a,3,4,5,6,6a, 6b,7,8,8a,8b,11a,12,12a,12b-hexadecahydro-1H-naphtho [2',1':4,5]indeno[2,1-b]furan-10-yl)-2-methylbutyl) carbamate, (Example 5) (75 mg, 0.15 mmol), N-methylmorpholine N-oxide hydrate (41 mg, 0.30 mmol), tetrapropylammonium perruthenate (1 mg, 0.3 mmol), and 60 mg of activated molecular seives were dissolved in 1 mL of dichloromethane. After stirring at room temperature for 2 h the solution was filtered and evaporated to give an oil that was purified by flash chromatography eluting with hexanes and ethyl acetate to provide 44 mg of tert-Butyl ((S)-2-methyl-4-((2aS,6aS,6bS,8aS,8bS,11aS,12aS,12bR)-6a,8a,9-trimethyl-4-oxo-2,2a,3,4,5,6,6a,6b,7,8,8a,8b,11a,12,12a, 12b-hexadecahydro-1H-naphtho[2',1':4,5]indeno[2,1-b] furan-10-yl)butyl)carbamate 57%. $^1$H NMR (400 MHz, CDCl$_3$) and $^{13}$C NMR (100 MHz, CDCl$_3$) were consistent. LC t$_r$=6.73 min (C-18 column, 5 to 95% acetonitrile/water over 6 min at 1.7 mL/min with detection 210 nm, at 23° C.). ES(pos)MS m/z 514 (M+H calcd for C$_{32}$H$_{52}$NO$_4$ requires 514).

Step 2: tert-Butyl ((S)-2-methyl-4-((2aS,6aS,6bS,8aS, 8bS,11aS,12aS,12bR)-6a,8a,9-trimethyl-4-oxo-2,2a,3,4,5,6, 6a,6b,7,8,8a,8b,11a,12,12a,12b-hexadecahydro-1H-naphtho [2',1':4,5]indeno[2,1-b]furan-10-yl)butyl)carbamate (100 mg, 0.195 mmol), ethanolamine (14.1 μL, 0.23 mmol), in 1.0 mL of methanol was treated with sodium cyanoborohydride (13.5 mg, 0.21 mmol) and allowed to stir at room temperature for 18 h. The reaction was then made basic with 1N NaOH and extracted with ethyl acetate. The ethyl acetate extract was washed with water, brine, dried over anhy. MgSO$_4$, filtered and concentrated in vacuo. The residue was purified by flash chromatography eluting with methanol and dichloromethane. The appropriate fractions were collected and concentrated in vacuo to provide 31.3 mg of the title compound as a white solid, 29%. $^1$H NMR (400 MHz, CDCl$_3$) and $^{13}$C NMR (100 MHz, CDCl$_3$) were consistent. LC t$_r$=4.15 min (C-18 column, 5 to 95% acetonitrile/water over 6 min at 1.7 mL/min with detection 210 nm, at 23° C.). ES(pos)MS m/z 559 (M+H calcd for C$_{34}$H$_{59}$N$_2$O$_4$ requires 543).

Example 11. 2-(((2aS,6aS,6bS,8aS,8bS,11aS,12aS, 12bR)-10-((S)-4-amino-3-methylbutyl)-6a,8a,9-trimethyl-2,2a,3,4,5,6,6a,6b,7,8,8a,8b,11a,12,12a,12b-hexadecahydro-1H-naphtho[2',1':4,5]indeno[2,1-b] furan-4-yl)amino)ethanol dihydrochloride

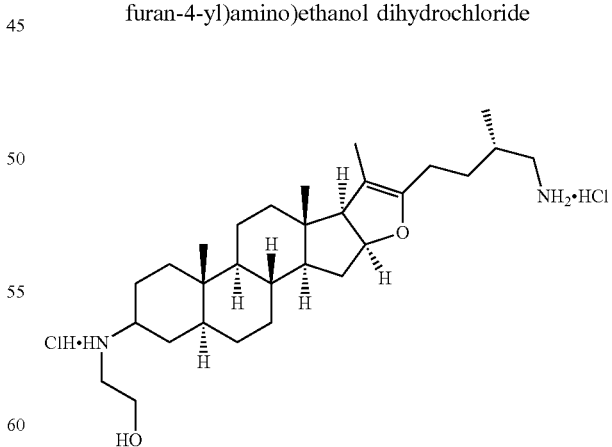

tert-Butyl ((2S)-4-((2aS,6aS,6bS,8aS,8bS,11aS,12aS, 12bR)-4-((2-hydroxyethyl)amino)-6a,8a,9-trimethyl-2,2a,3, 4,5,6,6a,6b,7,8,8a,8b,11a,12,12a,12b-hexadecahydro-1H-naphtho[2',1':4,5]indeno[2,1-b]furan-10-yl)-2-methylbutyl) carbamate (Example 10) (15 mg, 0.27 mmol) was dissolved in 0.5 mL of 4N HCl in dioxane and then stirred at room temperature for 0.5 h. The solvent was removed in vacuo and to afford 10.2 mg of the title compound as a white solid, 72%. LC $t_r$=2.62 min (C-18 column, 5 to 95% acetonitrile/water over 6 min at 1.7 mL/min with detection 210 nm, at 23° C.). ES(pos)MS m/z 459 (M+H calcd for $C_{29}H_{51}N_2O_4$ requires 459).

The compounds were tested in a well-established in vitro model of skeletal muscle, namely fully differentiated, post-mitotic C2C12 skeletal myotubes. Mouse C2C12 myoblasts may be obtained from ATCC (CRL-1772) and maintained at 37° C. and 5% $CO_2$ in Dulbecco's modified Eagle's medium (ATCC #30-2002) containing antibiotics (100 units/mL penicillin, 100 mg/mL streptomycin sulfate) and 10% (v/v) fetal bovine serum (FBS). Myoblasts were set up for experiments on day 0 in 6-well plates at a density of 2.5×10⁵ cells/well. On day 2, myoblasts were induced to differentiate into myotubes by replacing 10% FBS with 2% horse serum (HS). On day 7, myotubes were rinsed once with PBS, and then 2% HS was replaced with 10% FBS. The vehicle (0.1% DMSO) or varying concentrations of test compound were added directly to the media. After 48 h incubation, myotube protein content and size were measured.

To determine myotube protein content, myotubes were washed with ice cold PBS, scraped into lysis buffer (10 mM Tris-HCl, pH 7.6, 100 mM NaCl, and 1% (w/v) SDS, complete Mini protease inhibitor cocktail (Roche), and a 1:100 dilution of phosphatase inhibitor cocktail 3 (Sigma)), and then lysed with 10 passes through a 22-gauge needle. An aliquot of each myotube lysate sample was then used to determine protein concentration by the BCA kit (Pierce). Compounds of the invention significantly increased total cellular protein in a dose-dependent manner, indicating myotube hypertrophy. To determine myotube size, myotubes were subjected to immunofluorescence staining with anti-troponin primary antibody and a fluorescent secondary antibody. Myotubes were then imaged on an Olympus IX-71 microscope equipped with a DP-70 camera and epifluorescence filters. Image analysis was performed using ImageJ software. Compounds of the invention increased myotube diameter in a dose-dependent manner, indicating myotube hypertrophy. Taken together, these data indicate that compounds of the invention stimulate skeletal myotube hypertrophy. Data for individual compounds exemplary of the invention are shown in the following table:

| Example # | 0.03 µM | 0.1 µM | 0.3 µM | 1 µM | 3 µM |
|---|---|---|---|---|---|
| 1 | 1.0 ± 1.1 | 5.6 ± 3.3 | 10.7 ± 1.9** | 16.7 ± 1.3*** | 18.1 ± 0.5*** |
| 2 | 3.2 ± 2.1 | 3.2 ± 3.0 | 4.9 ± 3.9 | 8.3 ± 3.8* | 10.8 ± 3.0** |
| 3 | 3.8 ± 1.8 | 6.7 ± 2.4* | 9.2 ± 2.4** | 16.4 ± 1.3*** | 17.9 ± 0.7*** |
| 4 | 4.3 ± 1.6 | 4.0 ± 2.1 | 11.2 ± 2.3** | 13.4 ± 1.5*** | 11.4 ± 2.9** |
| 5 | 2.4 ± 2.1 | 2.7 ± 2.0 | 3.2 ± 1.5 | 13.3 ± 3.3** | 7.3 ± 2.6* |
| 6 | 1.1 ± 0.8 | −0.1 ± 3.1 | 4.2 ± 3.2 | 10.9 ± 3.1** | 9.0 ± 1.6* |
| 7 | −0.9 ± 1.5 | 0.5 ± 1.9 | 11.6 ± 2.3** | 11.0 ± 1.9** | 12.2 ± 3.2** |
| 8 | 0.5 ± 2.1 | 5.0 ± 1.9 | 9.7 ± 0.7** | 10.7 ± 1.6** | 9.1 ± 1.2** |
| 9 | −1.5 ± 2.3 | 1.2 ± 0.7 | 8.6 ± 2.5** | 6.2 ± 2.1** | 6.9 ± 2.6** |
| 10 | 10.3 ± 2.7** | 10.6 ± 2.2** | 15.0 ± 2.2*** | 12.9 ± 1.6*** | 16.1 ± 1.6*** |
| 11 | −1.8 ± 2.0 | 7.7 ± 1.5** | 6.3 ± 1.9* | 8.8 ± 2.1** | 4.9 ± 1.1* |

**P ≤ 0.01
***P ≤ 0.001

Compounds of the invention were also tested in vivo in an established mouse model for muscular atrophy. Male C57BL/6 mice (8-10 weeks old) were administered i.p. injections of vehicle (corn oil) or 10 mg/kg test compound twice a day for 7 days. After 1 day of i.p. injections, one tibialis anterior (TA) muscle in each mouse was immobilized with a metal clip to induce skeletal muscle atrophy, as described previously (Dyle et al., Journal of Biological Chemistry 289: 14913-14924, 2014). In each mouse, the contralateral TA muscle remained mobile and served as a non-atrophied intrasubject control. After 7 days of i.p injections (6 days of unilateral TA immobilization), bilateral TA muscles were harvested and weighed. In each mouse, the amount of skeletal muscle loss in the immobilized TA muscle was determined by normalizing the weight of the immobilized TA muscle to the weight of the contralateral mobile (control) TA muscle. The data below are means±SEM from 12-13 mice per condition. table:

| Example number | % Muscle Loss (Mean ± SEM) |
|---|---|
| Vehicle (Corn Oil) | 12.5 ± 1.7 |
| 1. | 4.8 ± 1.4 |
| 2. | 8.6 ± 1.8 |
| 3. | 8.3 ± 1.9 |

The invention claimed is:

1. A compound of formula I

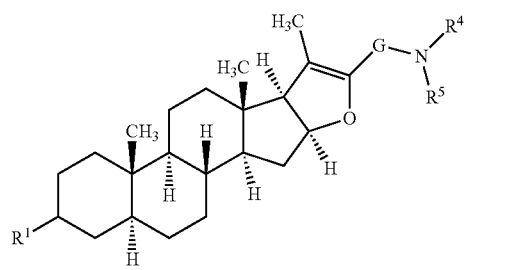

wherein:
$R^1$ is chosen from $OR^2$ and $NHR^3$;
$R^2$ is acetyl;
$R^3$ is chosen from $-(CH_2)_n OH$ and $-(CH_2CH_2O)_n H$;
G is $(C_2-C_{10})$hydrocarbyl;
$R^4$ is chosen from H, ethyl, n-propyl, and isopropyl; and
$R^5$ is chosen from H, alkyl, cycloalkyl, polycycloalkyl, alkenyl, alkynyl, aryl and combinations thereof, wherein alkyl is chosen from ethyl, n-propyl, isopropyl, n-butyl, isobutyl, s-butyl, t-butyl, n-pentyl, isopentyl, s-pentyl, neopentyl, hexyl, heptyl, octyl, nonyl, and decyl; fluoro($C_1$-$C_6$)alkyl, and —C(=O)$R^6$, wherein $R^6$ is chosen from H, alkyl, cycloalkyl, polycycloalkyl, alkenyl, alkynyl, and combinations thereof, wherein alkyl is chosen from hexyl, heptyl, octyl, nonyl, and decyl; —O—($C_1$-$C_{10}$)hydrocarbyl, —NH—($C_1$-$C_{10}$)hydrocarbyl, substituted aryl, substituted arylalkyl, heterocyclyl, substituted heteroaryl, heteroarylalkyl, substituted heteroarylalkyl, —NH-(substituted aryl), —NH-(substituted arylalkyl), —NH-(heterocyclyl), and —NH-(substituted heteroaryl);

wherein substituents on aryl and heteroaryl are chosen from halogen, halo($C_1$-$C_6$)alkyl, ($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, phenyl, heteroaryl, benzenesulfonyl, hydroxy, halo($C_1$-$C_6$)alkoxy, ($C_1$-$C_6$)oxaalkyl, carboxy, ($C_1$-$C_6$)alkoxycarbonyl, ($C_1$-$C_6$)alkoxycarbonylamino, carboxamido, ($C_1$-$C_6$)alkylaminocarbonyl, cyano, acetoxy, nitro, amino, ($C_1$-$C_6$)alkylamino, di($C_1$-$C_6$)alkylamino, di($C_1$-$C_6$)alkylamino($C_1$-$C_6$)alkyl, mercapto, ($C_1$-$C_6$)alkylthio, ($C_1$-$C_6$)alkylsulfone, sulfonylamino, ($C_1$-$C_6$)alkylsulfinyl, ($C_1$-$C_6$)alkylsulfonyl, ($C_1$-$C_6$)acylamino($C_1$-$C_6$)alkyl, ($C_1$-$C_6$)acylamino, amidino, heterocyclyl, phenoxy, benzyloxy, heteroaryloxy, hydroxyimino, alkoxyimino, aminosulfonyl, guanidino and ureido; and n is 2-6.

2. A compound according to claim 1 wherein $R^1$ is $NHR^3$.

3. A compound according to claim 2 wherein $R^3$ is —$CH_2CH_2OH$.

4. A compound according to claim 1 wherein $R^1$ is $OR^2$.

5. A compound according to claim 4 wherein the carbon to which $R^1$ is attached is of the (S) absolute configuration.

6. A compound according to claim 1 wherein G is linear or branched ($C_4$-$C_7$)alkyl.

7. A compound according to claim 6 wherein G is branched ($C_5$)alkyl.

8. A compound according to claim 7 wherein G is —$CH_2CH_2CH(CH_3)CH_2$—.

9. A compound of formula I

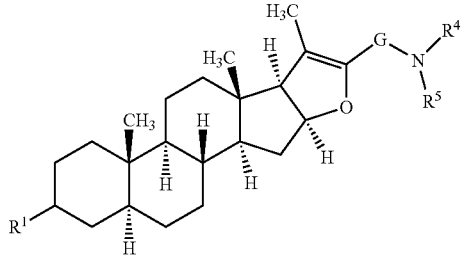

wherein:
$R^1$ is chosen from $OR^2$ and $NHR^3$;
$R^2$ is H or acetyl;
$R^3$ is chosen from —$(CH_2)_n$OH and —$(CH_2CH_2O)_n$H;
G is ($C_2$-$C_{10}$)hydrocarbyl;
$R^4$ is methyl; and
$R^5$ is chosen from fluoro($C_1$-$C_6$)alkyl, and —C(=O)$R^6$,
wherein $R^6$ is chosen from —O—($C_1$-$C_{10}$)hydrocarbyl, —NH—($C_1$-$C_{10}$)hydrocarbyl, —NH-(substituted aryl), —NH-(substituted arylalkyl), —NH-(heterocyclyl), and —NH-(substituted heteroaryl);

wherein substituents on aryl and heteroaryl are chosen from halogen, halo($C_1$-$C_6$)alkyl, ($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, phenyl, heteroaryl, benzenesulfonyl, hydroxy, halo($C_1$-$C_6$)alkoxy, ($C_1$-$C_6$)oxaalkyl, carboxy, ($C_1$-$C_6$)alkoxycarbonyl, ($C_1$-$C_6$)alkoxycarbonylamino, carboxamido, ($C_1$-$C_6$)alkylaminocarbonyl, cyano, acetoxy, nitro, amino, ($C_1$-$C_6$)alkylamino, di($C_1$-$C_6$)alkylamino, di($C_1$-$C_6$)alkylamino($C_1$-$C_6$)alkyl, mercapto, ($C_1$-$C_6$)alkylthio, ($C_1$-$C_6$)alkylsulfone, sulfonylamino, ($C_1$-$C_6$)alkylsulfinyl, ($C_1$-$C_6$)alkylsulfonyl, ($C_1$-$C_6$)acylamino($C_1$-$C_6$)alkyl, ($C_1$-$C_6$)acylamino, amidino, heterocyclyl, phenoxy, benzyloxy, heteroaryloxy, hydroxyimino, alkoxyimino, aminosulfonyl, guanidine and ureido; and n is 2-6.

10. A compound according to claim 1 wherein $R^4$ is H.

11. A compound according to claim 1 wherein $R^5$ is chosen from H, ethyl, n-propyl, isopropyl, n-butyl, isobutyl, s-butyl, t-butyl, n-pentyl, isopentyl, s-pentyl, neopentyl, hexyl and fluoro($C_1$-$C_6$)alkyl.

12. A compound according to claim 1 wherein $R^5$ is H.

13. A compound according to claim 1 wherein $R^5$ is chosen from ethyl, propyl, butyl and their fluorinated congeners.

14. A compound according to claim 1 wherein $R^5$ is —C(=O)$R^6$.

15. A compound according to claim 14 wherein $R^6$ is chosen from H, alkyl, cycloalkyl, polycycloalkyl, alkenyl, alkynyl, aryl and combinations thereof, wherein alkyl is chosen from hexyl, heptyl, octyl, nonyl, and decyl; and —O—($C_1$-$C_{10}$)hydrocarbyl.

16. A compound according to claim 15 wherein $R^6$ is —O($C_1$-$C_6$)alkyl.

17. A pharmaceutical composition comprising a pharmaceutically acceptable carrier and a compound according to claim 1.

18. A method for reducing skeletal muscle atrophy or promoting skeletal muscle hypertrophy, said method comprising administering to an animal a compound according to claim 1.

19. A method for reducing skeletal muscle atrophy or promoting skeletal muscle hypertrophy, said method comprising administering to an animal a compound according to claim 9.

20. A compound of formula I

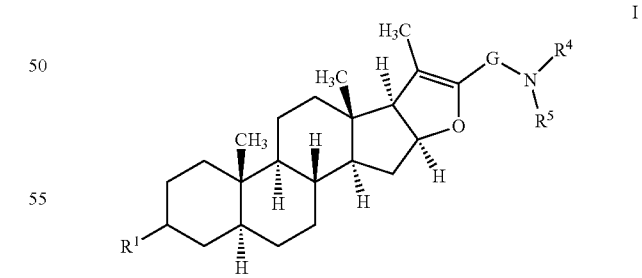

wherein:
$R^1$ is chosen from $OR^2$ and $NHR^3$;
$R^2$ is H or acetyl;
$R^3$ is chosen from $(CH_2)_n$OH and —$(CH_2CH_2O)_n$H;
G is ($C_2$-$C_{10}$)hydrocarbyl;
$R^4$ is H; and
$R^5$ is chosen from octyl, nonyl, and decyl; fluoro($C_1$-$C_6$)alkyl, and —C(=O)$R^6$, wherein $R^6$ is chosen from octyl, nonyl, and decyl; —O—($C_1$-$C_{10}$)hydrocarbyl, —NH—($C_1$-$C_{10}$)hydrocarbyl, substituted heteroaryl, heteroarylalkyl, substituted heteroarylalkyl, —NH-(substituted aryl), —NH-(substituted arylalkyl), —NH-(heterocyclyl), and —NH-(substituted heteroaryl);

wherein substituents on aryl and heteroaryl are chosen from halogen, halo($C_1$-$C_6$)alkyl, ($C_1$-$C_6$)acyl, ($C_1$-$C_6$)alkoxy($C_1$-$C_6$)alkyl, hydroxy($C_1$-$C_6$)alkyl, phenyl, heteroaryl, benzenesulfonyl, hydroxy, halo($C_1$-$C_6$)alkoxy, ($C_1$-$C_6$)oxaalkyl, carboxy, ($C_1$-$C_6$)alkoxycarbonyl, ($C_1$-$C_6$)alkoxycarbonylamino, carboxamido, ($C_1$-$C_6$)alkylaminocarbonyl, cyano, acetoxy, nitro, amino, ($C_1$-$C_6$)alkylamino, di($C_1$-$C_6$)alkylamino, di($C_1$-$C_6$)alkylamino($C_1$-$C_6$)alkyl, mercapto, ($C_1$-$C_6$)alkylthio, ($C_1$-$C_6$)alkylsulfone, sulfonylamino, ($C_1$-$C_6$)alkylsulfinyl, ($C_1$-$C_6$)alkylsulfonyl, ($C_1$-$C_6$)acylamino($C_1$-$C_6$)alkyl, ($C_1$-$C_6$)acylamino, amidino, heterocyclyl, phenoxy, benzyloxy, heteroaryloxy, hydroxyimino, alkoxyimino, aminosulfonyl, guanidino and ureido, with the proviso that both of $R^2$ and $R^5$ are not H; and n is 2-6.

21. A compound according to claim 20 wherein $R^1$ is $OR^2$.

22. A compound according to claim 21 wherein the carbon to which $R^1$ is attached is of the (S) absolute configuration.

23. A compound according to claim 20 wherein G is linear or branched ($C_4$-$C_7$)alkyl.

24. A compound according to claim 23 wherein G is branched ($C_5$)alkyl.

25. A compound according to claim 24 wherein G is —$CH_2CH_2CH(CH_3)CH_2$—.

26. A compound according to claim 20 wherein $R^5$ is chosen from fluoro($C_1$-$C_6$)alkyl, and —C(=O)$R^6$.

27. A compound according to claim 26 wherein $R^5$ is —C(=O)$R^6$ and $R^6$ is chosen from O—($C_1$-$C_{10}$)hydrocarbyl, —NH—($C_1$-$C_{10}$)hydrocarbyl, substituted heteroaryl, heteroarylalkyl, substituted heteroarylalkyl, —NH-(substituted aryl), —NH-(substituted arylalkyl), —NH-(heterocyclyl), and —NH-(substituted heteroaryl).

28. A compound according to claim 27 wherein $R^6$ is —O($C_1$-$C_6$)alkyl.

* * * * *